(12) United States Patent
Blanchard et al.

(10) Patent No.: US 11,096,410 B2
(45) Date of Patent: Aug. 24, 2021

(54) COMPOSITION FOR USE IN THE PREVENTION AND/OR TREATMENT OF SKIN CONDITIONS AND SKIN DISEASES

(71) Applicant: NESTEC S.A., Vevey (CH)

(72) Inventors: Carine Blanchard, Le Mont-sur-Lausanne (CH); Chiara Nembrini, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/071,539

(22) PCT Filed: Jan. 26, 2017

(86) PCT No.: PCT/EP2017/051582
§ 371 (c)(1),
(2) Date: Jul. 20, 2018

(87) PCT Pub. No.: WO2017/129642
PCT Pub. Date: Aug. 3, 2017

(65) Prior Publication Data
US 2019/0029306 A1    Jan. 31, 2019

(30) Foreign Application Priority Data
Jan. 26, 2016 (EP) .................................... 16152760

(51) Int. Cl.
| | | |
|---|---|---|
| *A23L 33/21* | (2016.01) | |
| *A23L 33/00* | (2016.01) | |
| *A23L 33/135* | (2016.01) | |
| *A61P 17/00* | (2006.01) | |
| *A61K 31/702* | (2006.01) | |
| *A61K 35/00* | (2006.01) | |

(52) U.S. Cl.
CPC .............. *A23L 33/21* (2016.08); *A23L 33/135* (2016.08); *A23L 33/40* (2016.08); *A61K 31/702* (2013.01); *A61P 17/00* (2018.01); *A23V 2002/00* (2013.01); *A23V 2200/318* (2013.01); *A23V 2250/284* (2013.01); *A61K 2035/115* (2013.01)

(58) Field of Classification Search
CPC .......... A23L 33/21; A23L 33/135; A23L 33/40
See application file for complete search history.

(56) References Cited

U.S. PATENT DOCUMENTS

| | | | |
|---|---|---|---|
| 2011/0064707 A1* | 3/2011 | Rochat ................. | A61K 31/702 424/93.45 |
| 2012/0171166 A1* | 7/2012 | Chow ..................... | A23L 33/40 424/93.4 |
| 2013/0251844 A1* | 9/2013 | Sprenger .............. | A61K 31/702 426/2 |
| 2014/0249103 A1 | 9/2014 | Buck et al. | |
| 2016/0271189 A1* | 9/2016 | Cutcliffe ................ | A61K 35/74 |

FOREIGN PATENT DOCUMENTS

| | | |
|---|---|---|
| EP | 2454948 | 5/2012 |
| EP | 2455387 | 5/2012 |
| EP | 2465508 | 6/2012 |
| WO | 2015071131 | 5/2015 |

OTHER PUBLICATIONS

MacFarlane et al. "Bacterial metabolism and health-related effects of galacto-oligosaccharides and other prebiotics" Journal of Applied Microbiology, 2008, vol. 104, pp. 305-344.
Nylund et al. "Severity of atopic disease inversely correlates with intestinal microbiota diversity and butyrate-producing bacteria" Allergy, 2015, vol. 70, pp. 241-244.
Lodge et al. "Breastfeeding and asthma and allergies: a systematic review and meta-analysis" Acta Paediatrica, 2015, vol. 104, pp. 38-53.
Li et al. "Microbial Composition and In Vitro Fermentation Patterns of Human Milk Oligosaccharides and Prebiotics Differ between Formula-Fed and Sow-Reared Piglets" J. Nutr., 2012, vol. 142, pp. 681-689.

* cited by examiner

*Primary Examiner* — Pancham Bakshi
(74) *Attorney, Agent, or Firm* — K&L Gates LLP

(57) ABSTRACT

The invention discloses a composition comprising oligosaccharide, for use in the prevention and/or treatment of skin conditions and/or skin diseases by increasing SCFA, in particular colonic propionate and butyrate. Said skin disease is in particular atopic dermatitis.

17 Claims, 3 Drawing Sheets

Figure 1:
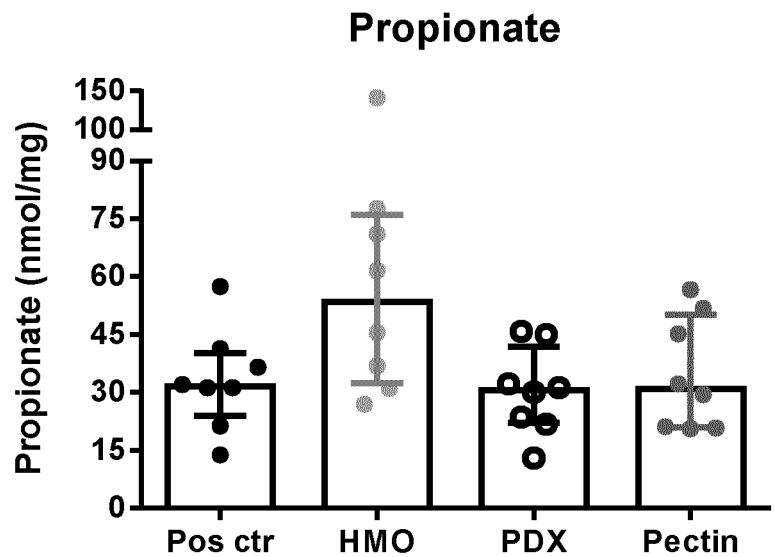

COMPOSITION FOR USE IN THE PREVENTION AND/OR TREATMENT OF SKIN CONDITIONS AND SKIN DISEASES

CROSS REFERENCE TO RELATED APPLICATIONS

The present application is a National Stage of International Application No. PCT/EP2017/051582, filed on Jan. 26, 2017, which claims priority to European Patent Application No. 16152760.1, filed on Jan. 26, 2016, the entire contents of which are being incorporated herein by reference.

This invention relates to a composition for use in the prevention and/or treatment of skin conditions, such as the promotion of skin health, and skin diseases, particularly atopic dermatitis.

BACKGROUND OF THE INVENTION

Atopic dermatitis is a chronic itchy skin disease that is common in children but may occur at any age. It is also known as eczema or atopic eczema.

A phenomenon of atopic dermatitis occurs as follows. Patches of sensitive skin flare up in a rash in response to certain triggers. These triggers vary from person to person. In the case of infants and young children, the list of common triggers to watch for includes cow's milk and other possible ingredients of infant formula such as wheat or soy. Atopic dermatitis can become a vicious cycle. Something irritates the child skin, making it red and inflamed. It itches, the child scratches it, and the skin becomes more inflamed. The outer protective layer of the skin is lost, and the affected area becomes even more sensitive to irritants and dries out easily. The infant continues to be exposed to whatever it was that triggered these episodes in the first place. The rash develops further and the cycle perpetuates itself.

There is no known single cause for atopic dermatitis and it may have an allergic or non-allergic origin. It probably reflects more than one condition. There are many theories regarding the underlying mechanisms. Current research is investigating the role of filaggrin gene mutations, defects in skin cells (keratinocytes), the immune system, skin surface microbes (bacteria, viruses and yeasts), and many other factors.

All skin conditions and skin diseases can affect the general population or the population of persons at risk of allergies or the population of allergic (hence sick) persons.

Such skin conditions and skin diseases, and in particular atopic dermatitis, are of particular importance for infants, babies or children as they have a sensitive skin that undergoes an intense growth and phases of multiplication, rendering it even more susceptible to skin diseases. The population of infants without history of allergies in their family, and who become allergic, is increasing.

Short Chain fatty acids (SCFAs) are especially produced by microbial fermentation of dietary fibres in the colon. High abundance of bacteria producing SCFA, particularly butyrate, has been shown to be linked to milder atopic eczema in infants (Nylund et al., "*Severity of Atopic disease inversely correlates with intestinal microbiota diversity and butyrate-producing bacteria*", European Journal of Allergy and clinical immunology, 2015).

Increasing SCFA is therefore an attractive target for use in the prevention and/or treatment of skin conditions, such as the promotion of skin health, and skin diseases, particularly atopic dermatitis.

However, orally administered SCFA may be unpalatable.

Alternative solutions more appropriate to infants and young children should therefore be developed.

From the foregoing, it may be seen that there is a need for an effective nutritional composition for the promotion of skin health, particularly in infants and young children, and which may be conveniently and safely administered.

There is a need for an improvement of skin conditions or skin diseases, such as atopic dermatitis, by a non-drug-based intervention that is compatible with fragile individuals like infants or babies.

There is a need for a long term effect in the reduction of the frequency, occurrence, severity and/or duration of such skin conditions and skin diseases. There is furthermore a need for an effect that becomes measurable "later in life", especially some years after the intervention.

There is a need for a food intervention to infants, babies and children, targeted at risks of allergy or not, that induces a reduction of allergic manifestations, especially on the skin.

There is a need for such intervention that induces the maintenance or the improvement of skin health.

SUMMARY OF THE INVENTION

The present inventors have found surprisingly that the administration of a mixture of specific oligosaccharides is particularly effective in the prevention and/or treatment of skin conditions and skin diseases, and in particular in the prevention and/or treatment of atopic dermatitis, and/or in the promotion of skin health.

Advantageously, the composition according to the invention is a nutritional composition.

Accordingly, in a first aspect, the present invention provides a composition comprising at least one fucosylated oligosaccharide and at least one N-acetylated oligosaccharide, for use in the prevention and/or treatment in infants or young children of skin conditions and skin diseases, preferably atopic dermatitis, by increasing propionate, in particular colonic propionate, production in such infants or young children.

In a particularly advantageous embodiment, the nutritional composition according to the invention comprises 2'-fucosyllactose (2-FL) and lacto-N-neotetraose (LNnT), and especially 2FL:LNnT in a weight ratio from 1:10 to 12:1.

In a second aspect, the present invention provides a composition comprising at least one N-acetylated oligosaccharide, at least one galacto-oligosaccharide and at least one sialylated oligosaccharide, for use in the prevention and/or treatment in infants or young children of skin conditions and skin diseases, preferably atopic dermatitis, by increasing colonic SCFA production, in particular colonic SCFA production, in such infants or young children.

In one embodiment, the nutritional composition according to the invention comprises an oligosaccharide mixture comprising from 0.1 to 4.0 wt % of the N-acetylated oligosaccharide(s), from 92.0 to 99.5 wt % of the galacto-oligosaccharide(s) and from 0.2 to 4.0 wt % of the sialylated oligosaccharide(s).

The composition comprises three different types of uses as nutritional composition. In the first case, individuals and particularly infants are healthy, without any risk of allergy because of no history of allergies in their family. In the second case, individuals and particularly infants are healthy, but at risk of allergy because of history of allergies in their family. In the third case, individuals and particularly infants are allergic, and hence sick. The first case is the preferred target according to the invention.

FIGURES

FIG. 1 represents the propionate production from caecum of mice fed with low-fiber diets and with low-fiber diets enriched with 5% of different tested fibers.

Abbreviations: Pos ctr=positive control; HMO=human milk oligosaccharides, 2FL+LNnT in a weight ratio of 1:1 were tested; PDX=polydextrose.

Figure 2:
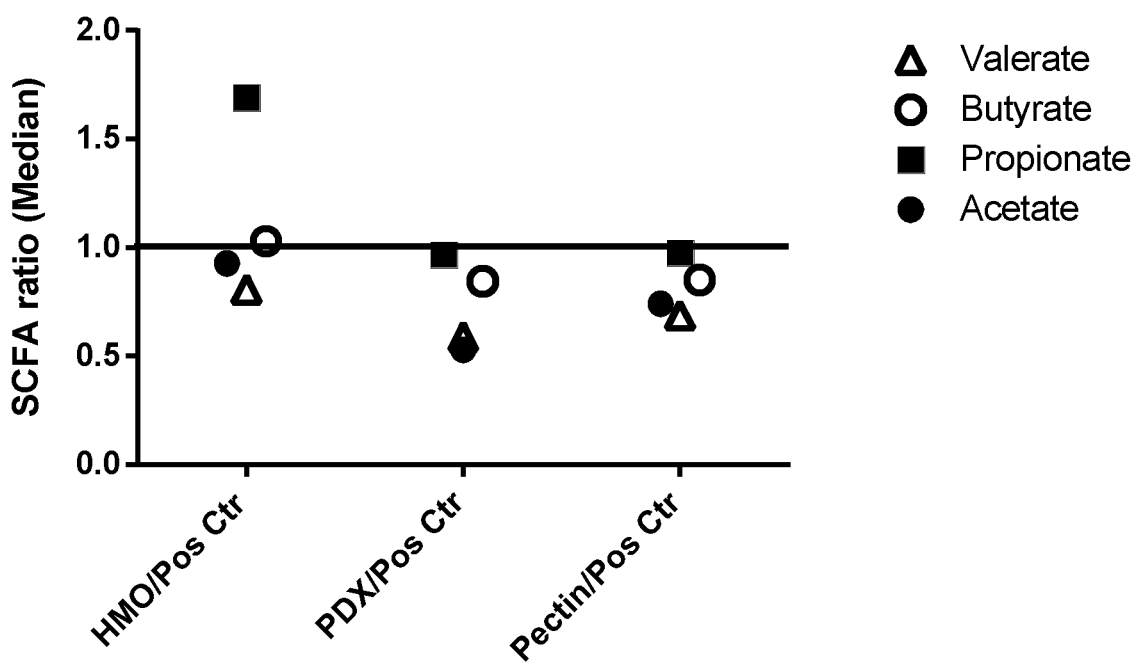

FIG. 2 represents the ratio of the median of each SCFA of fiber-enriched diet divided by the median of the positive control diet.

Abbreviations: Ctrl pos=positive control; HMO=human milk oligosaccharides, 2FL+LNnT in a weight ratio of 1:1 were tested; PDX=polydextrose.

Figure 3:
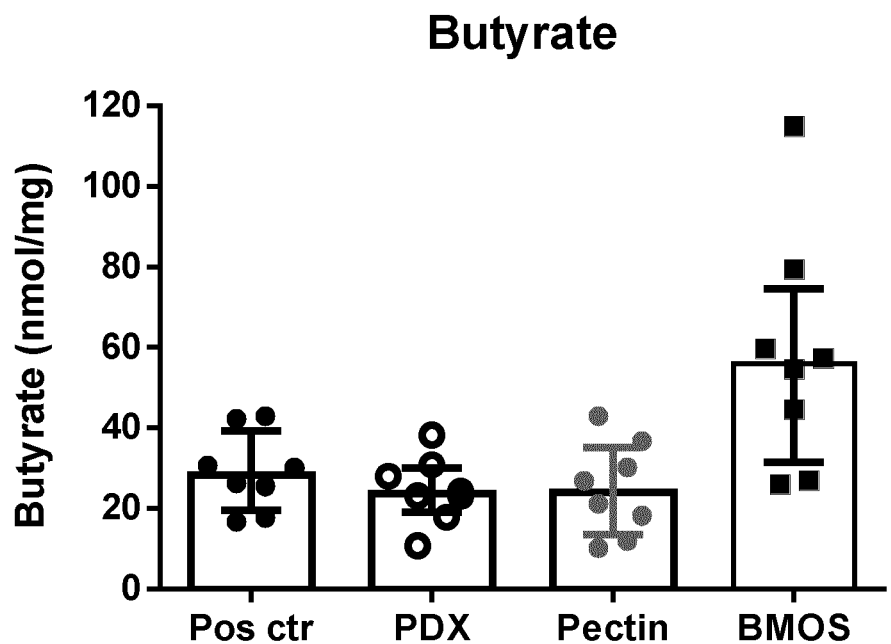

FIG. 3 represents the butyrate production from caecum of mice fed with low-fiber diets and with low-fiber diets enriched with 5% of different tested fibers.

Abbreviations: Pos ctr=positive control; BMOS=bovine milk oligosaccharides; PDX=polydextrose.

Figure 4:
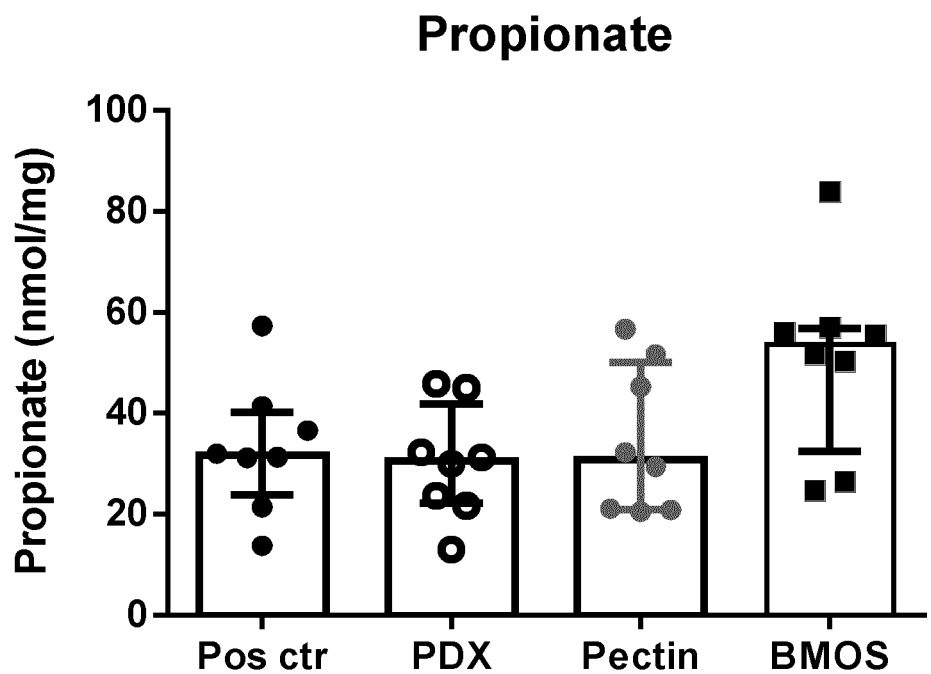

FIG. 4 represents the propionate production from caecum of mice fed with low-fiber diets and with low-fiber diets enriched with 5% of different tested fibers.

Abbreviations: Pos ctr=positive control; BMOS=bovine milk oligosaccharides; PDX=polydextrose.

Figure 5:
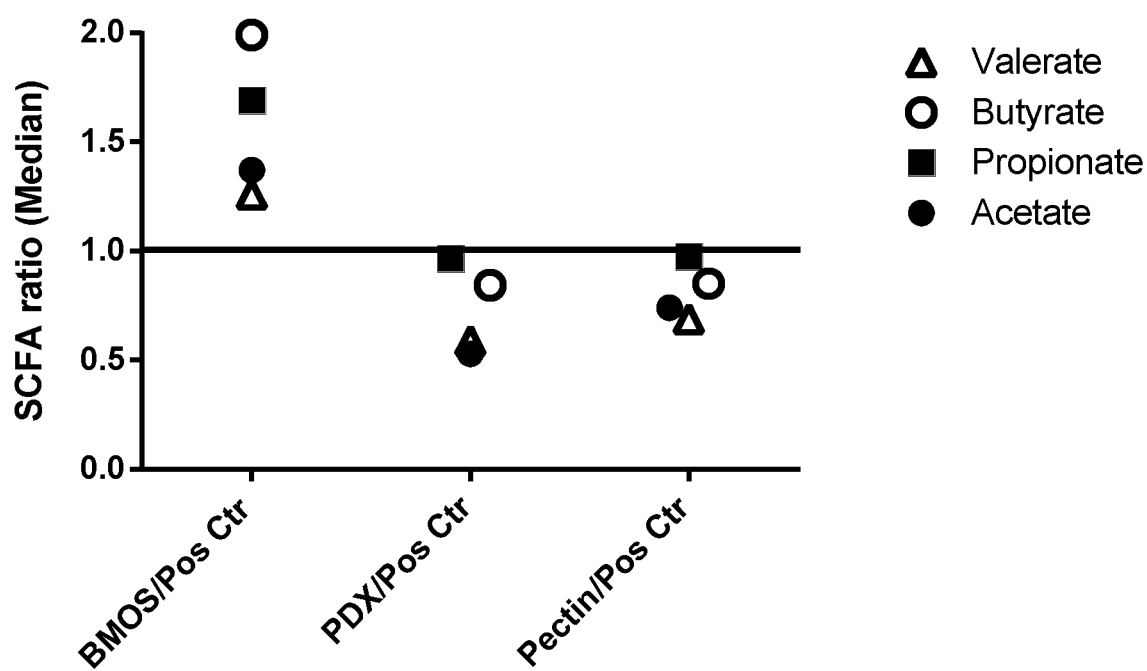

FIG. 5 represents the ratio of the median of each SCFA of fiber-enriched diet divided by the median of the positive control diet.

Abbreviations: Ctrl pos=positive control; BMOS=bovine milk oligosaccharide; PDX=polydextrose.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously. It may include a lipid or fat source, a carbohydrate source and/or a protein source. In a particular embodiment the nutritional composition is a ready-to-drink composition such as a ready-to-drink formula.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means or a mixture comprising components obtained by chemical and/or biological means (including for example purification and separation means), which mixture can be chemically identical to the mixture naturally occurring in mammalian milks or can comprise components which are identical to the components naturally occurring in mammalian milks (i.e. the synthetic nutritional composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 December 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk or infant formulas are substituted by other food in the diet of an infant or young child.

The expressions "days/weeks/months/years of life", "days/weeks/months/years after birth" and "days/weeks/months/years of birth" can be used interchangeably.

The expression "later in life" and "in later life" can be used interchangeably. They refer to effects measured in the individual (infant or young child) after the age of some weeks, some months or some years after birth, such as after the age of 6 months after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, 10 or 15 years of life. So the expression "later in life" might refer to an observation during infancy, during childhood, during the adolescent period, or during adulthood. Preferably it refers to an observation during childhood, during the adolescent period, or during adulthood.

The expression "health disorder(s)" encompass any health conditions and/or diseases and/or dysfunctions that affect the organism of an individual.

The term "SCFA" means short chain fatty acid(s).

The expression "increasing SCFA production" means that the amount of systemic and/or colonic SCFA, is higher in an individual fed with the nutritional composition according to the present invention in comparison with a standard composition and/or in comparison with a standard composition supplemented with common fibers like polydextrose or pectin. The SCFA may be propionate, butyrate, valerate and/or acetate. In a particular embodiment of the present invention, it is butyrate and/or propionate. The SCFA production may be measured by techniques known by the skilled person such as by Gas-Liquid Chromatography.

The expression "increasing colonic propionate production" means that the amount of propionate, when measured in the colon (or large intestine) or in a part thereof such as the caecum, is higher in an individual fed with the nutritional composition according to the present invention in comparison with a standard composition and/or in comparison with a standard composition supplemented with common fibers like polydextrose or pectin. The propionate production may be measured by techniques known by the skilled person such as by Gas-Liquid Chromatography.

The "mother's milk" should be understood as the breast milk or the colostrum of the mother.

The term "oligosaccharide" means a carbohydrate having a degree of polymerization (DP) ranging from 2 to 20 inclusive but not including lactose. In some embodiments of the invention, carbohydrate has DP ranging from 3 to 20.

The expressions "at least one N-acetylated oligosaccharide, one galacto-oligosaccharide and one sialylated oligosaccharide" and "at least one N-acetylated oligosaccharide, at least one galacto-oligosaccharide and at least one sialylated oligosaccharide" can be used interchangeably.

The expressions "oligosaccharide(s) mixture" or "mixture of oligosaccharide(s)" can be used interchangeably. The oligosaccharide(s) mixture according to one aspect of the invention comprises at least one N-acetylated oligosaccharide, at least one galacto-oligosaccharide and at least one sialylated oligosaccharide. The mixture may be made of one or several oligosaccharides of these different types, i.e. one or several N-acetylated oligosaccharide(s), one or several galacto-oligosaccharide(s) and one or several sialylated oligosaccharide(s). In some advantageous embodiments the oligosaccharides of the oligosaccharide mixture are bovine's milk oligosaccharides (or BMOs).

The term "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2'-FL (2'-fucosyllactose or 2-fucosyllactose or 2FL or 2-FL), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The expressions "galacto-oligosaccharide", "galactooligosaccharide" and "GOS" can be used interchangeably. They refer to an oligosaccharide comprising two or more galactose molecules which has no charge and no N-acetyl residue (i.e. they are neutral oligosaccharide). In a particular embodiment, said two or more galactose molecules are linked by a β-1,2, β-1,3, β-1,4 or β-1,6 linkage. In another embodiment, "galacto-oligosaccharide" and "GOS" also include oligosaccharides comprising one galactose molecule and one glucose molecule (i.e. disaccharides) which are linked by a β-1,2, β-1,3 or β-1,6 linkage.

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The terms "prebiotic", "fibre(s)" and "fiber(s)" can be used interchangeably. They refer to non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

The term "skin disease" means eczema or atopic dermatitis and other related skin issues.

The terms "Eczema" and "atopic dermatitis" (AD) are used interchangeably in the present invention. Eczema is an inflammatory, chronically relapsing, non-contagious and pruritic (itch causing) skin disorder. The skin of a patient with eczema overreacts easily to irritants, food, and environmental allergens and becomes red, flaky and very itchy (becomes a reactive skin). It also becomes vulnerable to surface infections caused by bacteria. The skin on the flexural surfaces of the joints is often affected in human subjects. Symptoms may vary from person to person but they are usually present as a red, inflamed, and itchy rash and can quickly develop into raised and painful bumps. The skin tends to be more sensitive and may thicken, crack, become dry or scale. Epidermal barrier dysfunction is considered to be an explanation on the physiopathology of atopic dermatitis. Changes in certain genes encoding structural proteins, epidermal proteases and protease inhibitors predispose to a defective epidermal barrier and increase the risk of developing atopic dermatitis. The strong association between both genetic barrier defects and environmental insults to the barrier with atopic dermatitis suggests that epidermal barrier dysfunction is a primary event in the development of this disease.

The term "prevention and/or treatment of skin diseases" means the prevention and the reduction of frequency and/or occurrence and/or severity and/or duration of skin diseases, i.e. atopic dermatitis and other related skin issues, in particular atopic dermatitis. Occurrence is related to the number of any skin disease. Frequency is related to the number of the same skin disease. This prevention encompasses the reduction of frequency and/or of severity of said skin diseases later in life. The term "later in life" encompasses the effect after the termination of the intervention. The effect "later in life" can be preferably 2 to 4 weeks, 2 to 12 months or years (e.g. 2, 5, 10 years) after the termination of said intervention.

The term "skin conditions" means conditions that irritate, clog or inflame the skin. Skin conditions can cause symptoms of skin diseases such as redness, swelling, burning and itching.

The term "prevention and/or treatment of skin conditions" means the promotion of skin health and/or the prevention of skin dehydration and/or the enhancement of the hydration of the skin and/or enhancement of skin barrier function and/or the reduction of skin rash, roughness and/or dryness. This prevention further encompasses the establishment of a phenotype, visible or hidden, that accompany the reduction of frequency, occurrence, severity and/or duration of said skin conditions later in life. "Barrier function" or "skin barrier protection" or "skin barrier function" is the function of the (epidermal) barrier to prevent the transition of agents, allergens, microorganisms, or water through the epidermal layer.

As used herein the term "enhancing the skin barrier function" means that the barrier function of the skin is strengthened. Thereby the transition of agents, allergens, microorganisms, or water through the epidermal layer is decreased. In particular, this enhancement of barrier function may be mediated by a reduction of the interstitial room between the epidermal cell layers. This may be effected by increasing the number of tight junctions or/and increasing the quality of the tight junctions between the epidermal cells and/or increased expression of protein of the epidermal differentiation complex (such as filaggrin, sprr, NICE, involucrin, loricrin).

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

First Aspect of the Invention

In a first aspect, the present invention therefore refers to a nutritional composition comprising at least one fucosylated oligosaccharide and at least one N-acetylated oligosaccharide, for use in the prevention and/or treatment in infants or young children of skin conditions and/or skin diseases, preferably atopic dermatitis, by increasing colonic propionate production in such infants or young children.

Without being bound by theory, the inventors of the present invention believe that the fucosylated oligosaccharide(s) and the N-acetylated oligosaccharide(s) act synergistically to surprisingly provide the above-mentioned health benefits. This particular combination of oligosaccharides would significantly increase the propionate production of an individual and therefore be useful for use in the prevention and/or treatment in infants or young children of skin conditions and skin diseases, preferably atopic dermatitis, by increasing colonic propionate production in such infants or young children.

The nutritional composition of the present invention comprises at least one fucosylated oligosaccharide. There can be one or several types of fucosylated oligosaccharide(s). The fucosylated oligosaccharide(s) can indeed be selected from the list comprising 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyl-lacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition of the present invention also comprises at least one the N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6.

In a preferred embodiment, the nutritional composition according to the invention comprises lacto-N-neotetraose (LNnT). In a particular embodiment, there is no other type of N-acetylated oligosaccharide than lacto-N-neotetraose (LNnT), i.e. the nutritional composition of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety. The N-acetylated oligosaccharide(s) may also be produced by biotechnological means based on microbial fermentation technology.

In a particularly advantageous embodiment of the present invention, the nutritional composition comprises 2'-fucosyllactose (2FL) and lacto-N-neotetraose (LNnT).

In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

In some embodiments the fucosylated oligosaccharide(s): N-acetylated oligosaccharide(s) (e.g. 2FL:LNnT) weight ratio in the nutritional composition of the present invention is from 1:10 to 12:1 such as from 1:7 to 10:1 or from 1:5 to 5:1, or from 2:1 to 5:1 or from 1:3 to 3:1, or from 1:2 to 2:1, or from 1:1 to 3:1, or from 1:5 to 1:0.5.

The fucosylated oligosaccharide(s) and the N-acetylated oligosaccharide(s) present into the nutritional composition of the present invention may be in a total amount of from 0.1 to 10 wt %, such as from 0.5 to 7 wt % or from 1 to 5 wt % of the nutritional composition before reconstitution with water. For reconstituted ready-to-drink formula target is from 0.01 to 1%, more preferably 0.05 to 0.7% or 0.1 to 0.5%.

The nutritional composition of the present invention may for example comprise:

fucosylated oligosaccharide(s) in a total amount of 0.2-5 g/L, for example 0.5-4.5 g/L or 1-4 g/L of the composition, or in a total amount of 0.13-3.48 g/100 g, for example 0.34-3.13 g/100 g or 0.69-2.78 g/100 g of composition on a dry weight basis; and/or N-acetylated oligosaccharide(s) in a total amount of 0.05-5 g/L, for example 0.1-2 g/L or 0.1-1 g/L of the composition, or in a total amount of 0.0.03-3.48 g/100 g, for example 0.07-1.4 g/100 g or 0.07-0.7 g/100 g of composition on a dry weight basis.

The nutritional composition according to the present invention may also comprise at least another oligosaccharide(s) (i.e. other than the fucosylated oligosaccharide(s) and N-acetylated oligosaccharide(s) necessarily present in the composition) and/or at least a fiber(s) and/or at least a precursor(s) of human milk oligosaccharide(s). The other oligosaccharide and/or fiber and/or precursor may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

In a particular embodiment, the composition according to the invention can comprise sialylated oligosaccharide(s). There can be one or several sialylated oligosaccharide(s). The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise sialylated oligosaccharide(s) in a total amount of from 0.05 to 5 g/L of, for example from 0.1 to 4 g/L, or from 0.3 to 2 g/L of the composition, or in a total amount of from 0.03 to 3.5 g/100 g, for example from 0.1 to 2 g or from 0.2 to 1 g/100 g of composition on a dry weight basis.

In a particular embodiment, the nutritional composition can also contain at least one BMO (bovine milk oligosaccharide). In a particular embodiment, the nutritional composition may additionally comprise an oligosaccharide mixture ("BMOS") that comprises from 0.1 to 4.0 wt % of N-acetylated oligosaccharide(s), from 92.0 to 99.5 wt % of the galacto-oligosaccharide(s) and from 0.2 to 4.0 wt % of the sialylated oligosaccharide(s). WO2006087391 and WO2012160080 provide some examples of production of a BMOS mixture.

In a more particular embodiment, the nutritional composition may additionally comprise an oligosaccharide mixture ("BMOS") that consists of from 0.1 to 4.0 wt % of N-acetylated oligosaccharide(s), from 92.0 to 99.5 wt % of the galacto-oligosaccharide(s) and from 0.2 to 4.0 wt % of the sialylated oligosaccharide(s).

In some particular embodiments of the present invention, the nutritional composition does not contain any sialylated oligosaccharide(s), any GOS and/or any bovine milk oligosaccharide.

The composition according to the present invention may optionally also comprise at least one precursor of human milk oligosaccharide. There can be one or several precursor(s). For example the precursor of human milk oligosaccharide is sialic acid, fucose or a mixture thereof. In some particular embodiments the composition comprises sialic acid. In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

The composition according to the invention can contain from 0 to 2.1 g of precursor(s) of human milk oligosaccharide per 100 g of composition on a dry weight basis, e.g. from 0 to 1.5 g or from 0 to 0.8 g or from 0 to 0.15 g of precursor(s) of human milk oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, Haemophilus, Moraxella and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm.

The nutritional composition of the present invention may also be used in an infant or a young child that was born by C-section or that was vaginally delivered.

In some embodiments the nutritional composition according to the invention can be for use before and/or during the weaning period.

In some embodiments the nutritional composition according to the invention is for use in infants or young children at risk of developing allergy. In some embodiments the nutritional composition of the present invention is for use in infants or young children born from allergic women. Indeed, scientific evidence continues to suggest that infants born to allergic mothers have a greater risk of becoming allergic later in life than infants born to mothers who are not allergic.

The nutritional composition can be administered (or given or fed) at an age and for a period that depends on the possibilities and needs.

Since the nutritional composition is mainly used for prevention purposes, it can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The present inventors have found that a specific HMOs intervention in an animal model significantly increased its propionate production in the caecum (a part of the colon). As mentioned in the background section, propionate is known to protect against skin disease.

The nutritional composition according to the present invention would therefore be useful in preventing and/or treating skin conditions and/or skin disease in an infant or a young child, by increasing colonic SFCA production in said infant or young children.

The health benefits targeted in the present invention may be obtained with the nutritional composition by increasing colonic propionate production in said infant or young child, especially the propionate production in the caecum. In a particular embodiment the propionate production is measured by Gas-Liquid Chromatography and it can be expressed in nmol/mg dry weight.

In a particular embodiment, the colonic propionate production is increased by at least 10%, or at least 15% or at least 20% or at least 30% or at least 40% or at least 50% or at least 60% in comparison to the colonic propionate production obtained with a nutritional composition without at least one fucosylated oligosaccharide and at least one N-acetylated oligosaccharide.

In a particular embodiment, the colonic propionate production is increased by at least 10%, or at least 15% or at least 20% or at least 30% or at least 40% or at least 50% or at least 60% or at least 70% in comparison to the colonic propionate production obtained with a nutritional composition supplemented with common fibers like polydextrose or pectin.

This represents a new clinical situation where prevention of allergy symptoms can be targeted in a new way.

Other Objects:

Another object of the present invention is the use of at least one fucosylated oligosaccharide and at least one N-acetylated oligosaccharide in the preparation of a nutritional composition for preventing and/or treating skin conditions and/or skin diseases, preferably atopic dermatitis, in infants or young children by increasing propionate, in particular colonic propionate, production in such infants or young children.

Another object of the present invention is a pharmaceutical composition comprising at least one fucosylated oligosaccharide and at least one N-acetylated oligosaccharide for preventing and/or treating skin conditions and/or skin diseases, preferably atopic dermatitis, in infants or young children by increasing propionate, in particular colonic propionate, production in such infants or young children.

Another object of the present invention is the use of at least one fucosylated oligosaccharide and at least one N-acetylated oligosaccharide for preventing and/or treating skin conditions and/or skin diseases, preferably atopic dermatitis, in infants or young children by increasing propionate, in particular colonic propionate, production in such infants or young children.

Another object of the present invention refers to a method for preventing and/or treating skin conditions and skin diseases, preferably atopic dermatitis, in infants or young children by increasing propionate, in particular colonic propionate, production in such infants or young children, said method comprising administering to said infant or young child a nutritional composition comprising at least one fucosylated oligosaccharide and at least one N-acetylated oligosaccharide.

In one embodiment, the eczema to be treated according to the present invention has allergic origin. In another embodiment, the eczema to be treated according to the present invention has non-allergic origin.

The different embodiments, details and examples previously described in the specification (e.g. related to the types and amounts of oligosaccharide, the nutritional composition, the administration, the targeted population . . . ,) also apply to all these other objects.

Second Aspect of the Invention

A first object of the present invention is therefore a nutritional composition comprising an oligosaccharide mixture, said oligosaccharide mixture comprising at least one N-acetylated oligosaccharide, at least one galacto-oligosaccharide and at least one sialylated oligosaccharide for use in the prevention and/or treatment in infants or young children of skin conditions and/or skin diseases, preferably atopic dermatitis, by increasing SCFA production, particularly colonic acetate, propionate and/or butyrate, in such infants or young children.

As illustrated in example 4, the inventors have found that the supplementation of an oligosaccharide mixture according to the present invention increased the SCFA production in an animal model, especially propionate and butyrate acetate. Without being bound by theory the inventors of the present invention believe that these particular oligosaccharides act synergistically to surprisingly provide a significant increased colonic SCFA production. Due to the known properties of SCFA, especially butyrate and propionate, such a supplementation could therefore be interestingly used to prevent and/or treat skin conditions and/or skin diseases, preferably atopic dermatitis in infants or young children.

The oligosaccharide mixture of the nutritional composition according to the invention comprises at least one N-acetylated oligosaccharide, at least one galacto-oligosaccharide and at least one sialylated oligosaccharide. As previously mentioned, there may be made of one or several oligosaccharides of these different types, i.e. one or several N-acetylated oligosaccharide(s), one or several galacto-oligosaccharide(s) and one or several sialylated oligosaccharide(s). The oligosaccharide mixture of the nutritional composition of the invention may be prepared from one or more animal milks. The milk may be obtained from any mammal, in particular from cows, goats, buffalos, horses, elephants, camels or sheep.

Alternatively the oligosaccharide mixture may be prepared by purchasing and mixing the individual components.

An N-acetylated oligosaccharide is an oligosaccharide having an N-acetylated residue. Suitable N-acetylated oligosaccharides of the oligosaccharide mixture of the nutritional composition according to the present invention include GalNAcβ1,3Galβ1,4Glc and Galβ1,6GalNAcβ1,3Galβ1,4Glc, but also any mixture thereof. The N-acetylated oligosaccharides may be prepared by the action of glucosaminidase and/or galactoaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerization (DP) from DP=1 onwards. Another option is the chemical conversion of keto-hexose (fructose) either free or bound to an oligosaccharide (e.g lactulose) into N-acetyl-hexosamine or an N-acetylhexosamine containing oligosaccharide as described in Wrodnigg, T. M, Dtutz, A. E, Angew. Chem. Int. Ed. 1999: 38: 827-828.

A galacto-oligosaccharide is an oligosaccharide comprising two or more galactose molecules which has no charge and no N-acetyl residue. Suitable galacto-oligosaccharides of the oligosaccharide mixture of the nutritional composition according to the present invention include Galβ1,3Galβ1,4Glc, Galβ1,6Galβ1,4Glc, Galβ1,3Galβ1,3Galβ1,4Glc, Galβ1,6Galβ1,6Galβ1,4Glc, Galβ1,3Galβ1,6Galβ1,4Glc, Galβ1,6Galβ1,3Galβ1,4Glc, Galβ1,6Galβ1,6Galβ1,6Glc, Galβ1,3Galβ1,3Glc, Galβ1,4Galβ1,4Glc and Galβ1,4Galβ1,4Galβ1,4Glc, but also any mixture thereof. Synthesized galacto-oligosaccharides such as Galβ1,6Galβ1,4Glc, Galβ1,6Galβ1,6Galβ1,6Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,4Galβ1,4Glc and Galβ1,4Galβ1,4Galβ1,4Glc and mixture thereof are commercially available under trademarks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycotransferases, such as galoctosyltransferases may be used to produce neutral oligosaccharides.

A sialylated oligosaccharide is an oligosaccharide having a sialic acid residue with associated charge. Suitable sialylated oligosaccharides of the oligosaccharide mixture of the nutritional composition according to the present invention include NeuAcβ2,3Galβ1,4Glc and NeuAcβ2,6Galβ1,4Glc, but also any mixture thereof. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP) from DP=1 onwards.

In one aspect of the invention, the nutritional composition comprises the oligosaccharide mixture in an amount from 2.5 to 15 wt %. Alternatively, the nutritional composition comprises the oligosaccharide mixture in an amount from 3 to 15 wt %, or in an amount from 3 to 10 wt %, or in an amount from 3.5 to 9.5 wt % or in an amount from 4 to 9 wt % or in an amount from 4.5 to 8.5 wt %, or in an amount from 5.0 to 7.5 wt % such as 5 wt %.

In some specific embodiments, the nutritional composition may comprise the oligosaccharide mixture in an amount from 0.5 to 3.1 g/100 kcal, or in an amount from 0.6 to 3.1 g/100 kcal, or in an amount from 0.6 to 2.0 g/100 kcal, or in an amount from 0.7 to 2.0 g/100 kcal, or in an amount from 0.8 to 1.8 g/100 kcal, or in an amount from 0.9 to 1.7 g/100 kcal, or in an amount from 1.0 to 1.5 g/100 kcal.

The nutritional composition of the present invention may comprise at least 0.01 wt % of N-acetylated oligosaccharide(s), at least 2.0 wt % of galacto-oligosaccharide(s) and at least 0.02 wt % of sialylated oligosaccharide(s).

In some embodiments, the nutritional composition according to the present invention may comprise at least 0.005 wt % or at least 0.01 wt %, or at least 0.02 wt %, or at least 0.03 wt %, or at least 0.04 wt %, or at least 0.05 wt %, or at least 0.06 wt % of N-acetylated oligosaccharide(s). In some embodiments, it may comprise from 0.005 to 0.06 wt % of N-acetylated oligosaccharide(s) such as from 0.005 to 0.05 wt % or from 0.005 to 0.04 or from 0.005 to 0.03 wt % or from 0.01 to 0.02 wt % of N-acetylated oligosaccharide(s). A particular example is an amount of 0.01 wt % of N-acetylated oligosaccharide(s).

In addition, the nutritional composition may comprise at least 2 wt %, or at least 3 wt %, or at least 4 wt %, or at least 5 wt %, or at least 5.5 wt %, or at least 6 wt % or at least 7 wt % or at least 8 wt % of galacto-oligosaccharide(s),In some embodiments, it may comprise from 4.5 to 8 wt % of galacto-oligosaccharide(s) such as from 4.75 to 6 wt % of galacto-oligosaccharide(s) or from 4.9 to 5 wt % or from 5.5 to 6.5 wt % of galacto-oligosaccharide(s). A particular example is an amount of 4.965 wt % of galacto-oligosaccharide(s).

Finally, the nutritional composition may comprise at least 0.01 wt %, or at least 0.02 wt %, or at least 0.03 wt %, or at least 0.04 wt %, or at least 0.05 wt %, or at least 0.06 wt %, or at least 0.07 wt %, or at least 0.08 wt % or at least 0.09 wt % of sialylated oligosaccharides. In some embodiments, it may comprise from 0.02 to 0.09 wt % of sialylated oligosaccharide(s) such as from 0.02 to 0.07 wt % of sialylated oligosaccharide(s), or from 0.02 to 0.05 wt % of sialylated oligosaccharide(s) or from 0.003 to 0.07 wt % of sialylated oligosaccharide(s). A particular example is an amount of 0.025 wt % of sialylated oligosaccharide(s).

In a particular embodiment, the nutritional composition according to the present invention may comprise from 0.01 to 0.07 wt % of N-acetylated oligosaccharide(s), from 2.0 to 8.0 wt % of galacto-oligosaccharide(s) and from 0.02 to 0.09 wt % of sialylated oligosaccharide(s).

In yet another particular embodiment, the nutritional composition according to the present invention may comprise from 0.01 to 0.03 wt % of N-acetylated oligosaccharide(s), 5.95 wt % galacto-oligosaccharide(s) and from 0.02 to 0.09 wt % of sialylated oligosaccharide(s).

In a particular embodiment, the nutritional composition may comprise from 0.0015 to 0.005 g/100 kcal of N-acetylated oligosaccharide(s), from 0.70 to 1.5 g/100 kcal of galacto-oligosaccharide(s) and from 0.0045 to 0.0085 g/100 kcal of sialylated oligosaccharide(s).

In another particular embodiment, the nutritional composition may comprise from 0.0015 to 0.0045 g/100 kcal of N-acetyl-oligosaccharide(s), from 0.74 to 1.2 g/100 kcal of galacto-oligosaccharide(s) and from 0.0045 to 0.0075 g/100 kcal of sialylated oligosaccharide(s).

In a particularly advantageous embodiment, the oligosaccharide mixture of the nutritional composition according to the invention comprises from 0.1 to 4.0 wt % of N-acetylated oligosaccharide(s), from 92.0 to 99.5 wt % of the galacto-oligosaccharide(s) and from 0.2 to 4.0 wt % of the sialylated oligosaccharide(s).

In a particularly advantageous embodiment, the oligosaccharide mixture of the nutritional composition according to the invention consists of from 0.1 to 4.0 wt % of N-acetylated oligosaccharide(s), from 92.0 to 99.5 wt % of the galacto-oligosaccharide(s) and from 0.2 to 4.0 wt % of the sialylated oligosaccharide(s).

The nutritional composition according to the invention may also contain other types of prebiotic (i.e. different and in addition to the oligosaccharides comprised in the oligosaccharide mixture as defined according to the present invention). Examples of other types of prebiotics include human milk oligosaccharides (HMOs) such as fucosylated oligosaccharides, oligofructose, fructo-oligosaccharides (FOS), inulin, xylooligosaccharides (XOS), polydextrose or any mixture thereof.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic strains include *Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus bulgari, Lactococcus lactis, Lactococcus diacetylactis, Lactococcus cremoris, Streptococcus salivarius, Streptococcus thermophilus, Bifidobacterium lactis, Bifidobacterium animalis, Bifidobacterium longum, Bifidobacterium breve, Bifidobacterium infantis, Bifidobacterium adolescentis* or any mixture thereof.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation K12, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, Haemophilus, Moraxella and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional compositions of the invention, and especially the infant formulas, generally contain a protein source, a carbohydrate source and a lipid source.

The nutritional composition according to the invention generally contains a protein source. The protein can be in an amount of from 1.5 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts.

Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s).

The nutritional composition of the invention (e.g. infant formula) may be prepared by blending together the protein source, the carbohydrate source and the fat source in appropriate proportions. Emulsifiers may be added if desired. Vitamins and minerals may be added at this point but are usually added later to avoid thermal degradation. Any lyophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger, e.g. a plate heat exchanger.

The liquid mixture may then by cooled to about 60° C. to about 85° C., for example by flash cooling. The liquid mixture may then be homogenized, for example in two stages at about 7 MPa to about 40 MPa in the first stage and about 2 MPa to about 14 MPa in the second stage. The homogenized mixture may then be further cooled to add any heat sensitive components such as vitamins and minerals. The pH and solids content of the homogenized mixture may be conveniently standardized at this point.

The homogenized mixture may be transferred to a suitable drying apparatus, such as spray drier or freeze drier, and may be converted to powder. The powder should have a moisture content of less than about 5% by weight.

The oligosaccharide mixture may be prepared by any suitable manner known in the art and added at different steps during the preparation of the nutritional composition of the present invention. The oligosaccharide mixture can be added directly to the nutritional composition (e.g. infant formula) by dry mixing (i.e. at the blending step). Alternatively, the oligosaccharide mixture can be added in liquid mixture prior to the thermal treatment to reduce the bacterial load. The individual components of the oligosaccharide mixture may also be added separately to the nutritional composition in which case the oligosaccharide mixture is preferably added in the liquid phase immediately prior to drying.

The nutritional composition according to the invention is for use in infants or young children. The infants or young children may be born term or preterm. In a particular embodiment the nutritional composition of the invention is for use in infants or young children that were born preterm. In a particular embodiment the nutritional composition of the invention is for use in preterm infants.

The nutritional composition of the present invention may also be used in an infant or a young child that was born by C-section or that was vaginally delivered.

In some embodiments the nutritional composition according to the invention can be for use before and/or during the weaning period.

In some embodiments the nutritional composition according to the invention is for use in infants or young children at risk of developing allergy. In some embodiments the nutritional composition of the present invention is for use in infants or young children born from allergic women. Indeed, scientific evidence continues to suggest that infants born to allergic mothers have a greater risk of becoming allergic later in life than infants born to mothers who are not allergic.

The nutritional composition can be administered (or given or fed) at an age and for a period that depends on the possibilities and needs.

When the nutritional composition is used for prevention purposes (prevention of a later in life health disorder), it can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

The oligosaccharide mixture present in the nutritional composition of the invention may be prepared from one or more animal milks. The milk can be obtained from any mammal, in particular from cows, goats, buffalos, horses, elephants, camels or sheep. In a specific embodiment, the oligosaccharides of the oligosaccharide mixture are bovine's milk oligosaccharides and can be obtained from cows, goats or buffalos' milk. In an advantageous embodiment, the oligosaccharides are obtained from cow's milk.

WO2006087391 and WO2012160080 provide some examples of production of a BMOs mixture.

The present inventors have found that the BMOs intervention in an animal model increased its colonic SCFA production, especially the caecum SCFA production and particularly butyrate and propionate. Since these SCFA have been shown to protect eczema, the nutritional composition according to the present invention would therefore be useful in prevention and/or treatment in infants or young children of skin conditions and/or skin diseases, preferably atopic dermatitis.

There may be one or several SCFA which production is increased. The SCFA may be propionate, butyrate, valerate and/or acetate. In a particular embodiment the SCFA is propionate and/or butyrate (i.e. propionate, butyrate or both).

So in a particular embodiment the prevention and/or treatment of skin conditions and skin diseases, preferably atopic dermatitis is obtained by increasing colonic propionate and/or butyrate production in said infant or young child.

In a particular embodiment the propionate and/or butyrate production is measured by Gas-Liquid Chromatography and it can be expressed in nmol/mg dry weight.

In a particular embodiment, the colonic butyrate production is increased by at least 10%, or at least 15% or at least 20% or at least 30% or at least 40% or at least 50% or at least 60% or at least 70% or at least 80% or at least 90% in comparison to the colonic butyrate production obtained with a nutritional composition without at least one N-acetylated oligosaccharide, at least one galacto-oligosaccharide and at least one sialylated oligosaccharide.

In a particular embodiment, the colonic butyrate production is increased by at least 10%, or at least 15% or at least 20% or at least 30% or at least 40% or at least 50% or at least 60% or at least 70% or at least 80% or at least 90% or at least 100% or more, in comparison to the colonic butyrate production obtained with a nutritional composition supplemented with common fibers like polydextrose or pectin.

In a particular embodiment, the colonic propionate production is increased by at least 10%, or at least 15% or at least 20% or at least 30% or at least 40% or at least 50% or at least 60% in comparison to the colonic propionate production obtained with a nutritional composition without at least one N-acetylated oligosaccharide, at least one galacto-oligosaccharide and at least one sialylated oligosaccharide.

In a particular embodiment, the colonic propionate production is increased by at least 10% or at least 15% or at least 20% or at least 30% or at least 40% or at least 50% or at least 60% or at least 70% in comparison to the colonic propionate production obtained with a nutritional composition supplemented with common fibers like polydextrose or pectin.

Other Objects:

Another object of the present invention is the use of an oligosaccharide mixture comprising at least one N-acetylated oligosaccharide, at least one galacto-oligosaccharide and at least one sialylated oligosaccharide in the preparation of a nutritional composition for the prevention and/or treatment in infants or young children of skin conditions and/or skin diseases, preferably atopic dermatitis, by increasing SCFA content, especially colonic butyrate and/or propionate.

Another object of the present invention is the use of an oligosaccharide mixture comprising at least one N-acetylated oligosaccharide, at least one galacto-oligosaccharide and at least one sialylated oligosaccharide (or the use of a nutritional composition comprising such an oligosaccharide mixture) for increasing SCFA production, especially in the colon, in an infant or a young child, especially butyrate and/or propionate.

Another object of the present invention is the use of a nutritional composition comprising an oligosaccharide mixture that comprises at least one N-acetylated oligosaccharide, at least one galacto-oligosaccharide and at least one sialylated oligosaccharide for the prevention and/or treatment in infants or young children of skin conditions and/or skin diseases, preferably atopic dermatitis, by increasing SCFA content, especially colonic butyrate and/or propionate.

Another object of the present invention is a pharmaceutical composition comprising an oligosaccharide mixture that comprises at least one N-acetylated oligosaccharide, at least one galacto-oligosaccharide and at least one sialylated oligosaccharide for the prevention and/or treatment in infants or young children of skin conditions and/or skin diseases, preferably atopic dermatitis, by increasing SCFA content, especially colonic butyrate and/or propionate.

Another object of the present invention is a method for the prevention and/or treatment in infants or young children of skin conditions and/or skin diseases, preferably atopic dermatitis, by increasing SCFA content, especially colonic butyrate and/or propionate, said method comprising administering to said infant or young child a nutritional composition comprising an oligosaccharide mixture that comprises at least one N-acetylated oligosaccharide, at least one galacto-oligosaccharide and at least one sialylated oligosaccharide.

Another object of the present invention is a method for increasing SCFA production in an infant or a young child, especially colonic butyrate and/or propionate, said method comprising administering to said infant or young child a nutritional composition comprising an oligosaccharide mixture that comprises at least one N-acetylated oligosaccharide, at least one galacto-oligosaccharide and at least one sialylated oligosaccharide.

Another object of the present invention is an oligosaccharide mixture comprising at least one N-acetylated oligosaccharide, at least one galacto-oligosaccharide and at least one sialylated oligosaccharide for use in a nutritional composition for an infant or a young child as a therapeutic agent that increases SCFA production in said infant or young child, especially colonic butyrate and/or propionate.

Another object of the present invention is a nutritional composition comprising at least one N-acetylated oligosaccharide, at least one galacto-oligosaccharide and at least one sialylated oligosaccharide, for use as a therapeutic agent that increases SCFA production in an infant or a young child, especially colonic butyrate and/or propionate.

The previously-mentioned embodiments and examples (e.g. related to the types and amounts of oligosaccharide, the nutritional composition, the administration, the targeted population . . . ) also apply for all these other objects.

Thus preferably the composition according to the invention (as described in both the first and second aspects) is for use in the reduction of frequency and/or occurrence and/or severity and/or duration of atopic dermatitis and/or for use in the promotion of skin health.

In an implementation, the composition according to the invention is for use in the promotion of skin health and/or for the prevention of skin dehydration and/or for use in the enhancement of the hydration of the skin and/or for use in the reduction of skin rash, roughness and dryness, and/or for use in enhancing the skin barrier function, and/or for use in the enhancement of the oral tolerance to allergens.

In one embodiment, the eczema to be treated according to the present invention has allergic origin. In another embodiment, the eczema to be treated according to the present invention has non-allergic origin.

The different embodiments, details and examples previously described in the specification (e.g. related to the types and amounts of oligosaccharide, the nutritional composition, the administration, the targeted population . . . ) also apply to all these other objects.

All the uses stated above are particularly intended for infants and young children. The compositions and uses as per the present invention are particularly suited for infants and children at risk of allergies, having a family history of allergies, or having already experienced some episodes of allergies (especially respiratory allergies or skin allergies). In one embodiment the composition and uses of the invention apply to teenagers or adults at risk of allergies or having experiences episodes of allergies (especially respiratory allergies or skin allergies).

The nutritional composition according to the invention may modulate the metabolism of endogenous microbiota leading to production of short-chain fatty acid, particularly propionate and butyrate, that will contribute to activate immune cells underlying the gut mucosa. Following triggering of the mucosal immune system, activated immune cells, immune-active compounds and/or immune mediators will circulate to distal locations, including skin, where they will exert immune modulatory activity. All together, these mechanisms will contribute to balance potential skin inflammatory conditions leading to improvement of related clinical manifestations such as dermatitis and eczema. Further, the inventors believe that such orchestrated immunity translates in lower skin sensitivity towards exogenous irritants and better skin barrier function leading to lower skin rash, roughness, and dryness, associated with reactive skin.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention.

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |

TABLE 1-continued an example of the composition of a nutritional composition (e.g. an infant formula) according to the present invention.

| Nutrients | | per 100 kcal | per litre |
|---|---|---|---|
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (μg) | | 8 | 50 |
| Se (μg) | | 2 | 13 |
| Vitamin A (μg RE) | | 105 | 700 |
| Vitamin D (μg) | | 1.5 | 10 |
| Vitamin E (mg TE) | | 0.8 | 5.4 |
| Vitamin K1 (μg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (μg) | | 9 | 60 |
| Pantothenic acid (mg) | | 0.45 | 3 |
| Vitamin B12 (μg) | | 0.3 | 2 |
| Biotin (μg) | | 2.2 | 15 |
| Choline (mg) | | 10 | 67 |
| Fe (mg) | | 1.2 | 8 |
| I (μg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Example 2

Description of the Study 5 week old females BALB/cByJ CRL mice from Charles River were split into several groups and fed during 6 weeks based on the following protocol:

Week 1: low-fiber diet (composition is detailed in table 2) for all groups

Weeks 2 to 6:

Control group (group A): low-fiber diet (same as for week 1)

Test groups (groups B-D): low-fiber diet (same as for week 1) supplemented with 5 wt % of a tested fiber (5% of the total low fiber diet was replaced by 5% of a tested fiber)

TABLE 2

| composition of the low fiber diet | |
|---|---|
| Major Nutrients | |
| Dry matter | 93.9% |
| Crude protein | 18.0% |
| Crude fat | 5.0% |
| Crude fiber | 0.3% |
| Crude ash | 3.5% |
| Nitrogen-free extract (NFE) | 67.1% |
| Gross energy | 17.7 MJ/kg |
| Metabol. energy | 16.1 MJ/kg |
| Starch | 42.5% |
| Amino acids | |
| Arginine | 0.76% |
| Lysine | 1.66% |
| Methionine | 0.60% |
| Methionine + cystine | 0.97% |
| Tryptophan | 0.28% |
| Threonine | 0.92% |

TABLE 2-continued composition of the low fiber diet

Major mineral elements

| Calcium | 0.62% |
|---|---|
| Phosphorus | 0.33% |
| Magnesium | 0.06% |
| Sodium | 0.24% |
| Potassium | 0.41% |
| Chlorine | 0.58% |

Trace elements

| Iron | 50 mg/kg |
|---|---|
| Zinc | 37 mg/kg |
| Copper | 6 mg/kg |
| Iodine | 0.6 mg/kg |
| Manganese | 12 mg/kg |
| Selenium | 0.22 mg/kg |

Vitamins added

| Vitamin A | 4'000 IE|UI|IU/kg |
|---|---|
| Vitamin D3 | 1'000 IE|UI|IU/kg |
| Vitamin E | 100 mg/kg |
| Vitamin K3 | 4 mg/kg |
| Vitamin B1 | 5 mg/kg |
| Vitamin B2 | 6 mg/kg |
| Vitamin B6 | 6 mg/kg |
| Vitamin B12 | 0.05 mg/kg |
| Nicotinic acid | 32 mg/kg |
| Pantothenic acid | 16 mg/kg |
| Folic acid | 2 mg/kg |
| Biotin | 0.2 mg/kg |
| Choline | 998 mg/kg |

The following fibers were tested:
HMO=human milk oligosaccharides. 2FL+LNnT were tested in a weight ratio 1:1
PDX=polydextrose
Pectin Table 3 provides a summary of the different tested groups and diets.

TABLE 3 tested groups and diets of the study

| Group | Group label | Diet | Sample size |
|---|---|---|---|
| A | Pos ctr or Ctrl pos | Low-fiber diet | 8 |
| B | HMO | Low-fiber diet + 5 wt % HMOs (=2FL + LNnT in a weight ratio 1:1) | 8 |
| C | PDX | Low-fiber diet + 5 wt % polydextrose | 8 |
| D | Pectin | Low-fiber diet + 5 wt % pectin | 8 |

After 6 weeks, the animals of each group were sacrificed and the content from caecum was collected. The SCFA production were measured by Gas-Liquid Chromatography (GLC; amounts of SCFA in nmol/mg dry weight). The following SCFA were measured: propionate, butyrate, valerate and acetate.

The measure was made based on the following protocol: SCFA in an acid solution (pH 2.0 to 3.0) were separated on a GLC column coated with a polar stationary phase. This allowed for minimal preparation of the sample (no derivatisation) and straightforward basic FID detection. SCFA were extracted from caecum using an acid phosphate buffer containing HgCl2 for inactivation of any residual bacterial activity and an internal standard (2,2 Dimethyl-butyric acid) for GLC analysis. After centrifugation, the sterile-filtered supernatant was ready for analysis by GLC. SCFA were measured simultaneously.

Median ratio values were calculated in order to compare the different fiber-enriched diets on SCFA production.

Findings

The production of propionate by HMO enriched diet was significantly increased (see FIG. 1). Its production was increased by around 69% in comparison to the positive control. Its production was increased by 73 and 75% in comparison to the pectin and PDX, respectively. This is very surprising since pectin is usually seen as a high-inducer of SCFA (Stark et al, J Nutr. 1993, In vitro production of short-chain fatty acids by bacterial fermentation of dietary fiber compared with effects of those fibers on hepatic sterol synthesis in rats; Yang et al, Anaerobe, 2013, In vitro characterization of the impact of selected dietary fibers on fecal microbiota composition and short chain fatty acid production).

FIG. 2 represents the ratio of the median of each tested SCFA of each fiber-enriched diet divided by the median of the positive control diet (i.e. low-fiber diet only). A ratio of 1 (black line) means that there is no difference between the enriched diet and the control diet. A ratio below 1 means that the corresponding SCFA is higher in the control diet when compared to the fiber-enriched diet whereas a ratio above a means that the corresponding SCFA is higher with the fiber-enriched diet than the control.

The PDX and Pectin enriched diets induced less SCFA release of all kinds. On the contrary the HMO enriched diets induced more propionate and butyrate release than the low-fiber diet. The HMO-enriched diet was the only one to promote the propionate with a so large difference contrary to the other kinds of SCFA, and contrary to the other tested fibers.

Example 3

An example of the composition of an infant formula comprising an oligosaccharide mixture according to the invention is given in the below table 4. The oligosaccharide mixture may for example comprise from 0.1 to 4.0 wt % of the N-acetylated oligosaccharide(s), from 92.0 to 99.5 wt % of the galacto-oligosaccharide(s) and from 0.2 to 4.0 wt % of the sialylated oligosaccharide(s).

TABLE 4 an example of the composition of a nutritional composition (e.g. an infant formula) according to the present invention

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |

TABLE 4-continued an example of the composition of a nutritional composition
(e.g. an infant formula) according to the present invention

| Nutrients | per 100 kcal | per litre |
|---|---|---|
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| Oligosaccharide Mixture (g) | 1.38 | 9.0 |

Example 4

Description of the Study 5 week old females BALB/cByJ CRL mice from Charles River were split into several groups and fed during 6 weeks based on the following protocol:
Week 1: low-fiber diet (composition is detailed in table 2) for all groups
Weeks 2 to 6:
  Control group (group A): low-fiber diet (same as for week 1)
  Test groups (groups B-D): low-fiber diet (same as for week 1) supplemented with 5 wt % of a tested fiber (5% of the total low fiber diet was replaced by 5% of a tested fiber)

TABLE 5 composition of the low fiber diet

| Major Nutrients | |
|---|---|
| Dry matter | 93.9% |
| Crude protein | 18.0% |
| Crude fat | 5.0% |
| Crude fiber | 0.3% |
| Crude ash | 3.5% |
| Nitrogen-free extract (NFE) | 67.1% |
| Gross energy | 17.7 MJ/kg |
| Metabol. energy | 16.1 MJ/kg |
| Starch | 42.5% |
| Amino acids | |
| Arginine | 0.76% |
| Lysine | 1.66% |
| Methionine | 0.60% |
| Methionine + cystine | 0.97% |
| Tryptophan | 0.28% |
| Threonine | 0.92% |
| Major mineral elements | |
| Calcium | 0.62% |
| Phosphorus | 0.33% |
| Magnesium | 0.06% |
| Sodium | 0.24% |
| Potassium | 0.41% |
| Chlorine | 0.58% |
| Trace elements | |
| Iron | 50 mg/kg |
| Zinc | 37 mg/kg |
| Copper | 6 mg/kg |
| Iodine | 0.6 mg/kg |
| Manganese | 12 mg/kg |

TABLE 5-continued composition of the low fiber diet

| Selenium | 0.22 mg/kg |
|---|---|
| Vitamins added | |
| Vitamin A | 4'000 IE|UI|IU/kg |
| Vitamin D3 | 1'000 IE|UI|IU/kg |
| Vitamin E | 100 mg/kg |
| Vitamin K3 | 4 mg/kg |
| Vitamin B1 | 5 mg/kg |
| Vitamin B2 | 6 mg/kg |
| Vitamin B6 | 6 mg/kg |
| Vitamin B12 | 0.05 mg/kg |
| Nicotinic acid | 32 mg/kg |
| Pantothenic acid | 16 mg/kg |
| Folic acid | 2 mg/kg |
| Biotin | 0.2 mg/kg |
| Choline | 998 mg/kg |

The following fibers were tested:
BMOs=bovine milk oligosaccharides: an oligosaccharide mixture comprising 99.3% of GOS, 0.2% of N-acetylated oligosaccharide and 0.5% sialylated oligosaccharide was tested
PDX=polydextrose
Pectin
Table 6 provides a summary of the different tested groups and diets.

TABLE 3 tested groups and diets of the study

| Group | Group label | Diet | Sample size |
|---|---|---|---|
| A | Pos ctr or Ctrl pos | Low-fiber diet | 8 |
| B | BMOS | Low-fiber diet + 5 wt % BMOs | 8 |
| C | PDX | Low-fiber diet + 5 wt % polydextrose | 8 |
| E | Pectin | Low-fiber diet + 5 wt % pectin | 8 |

After 6 weeks, the animals of each group were sacrificed and the content from caecum was collected. The SCFA production were measured by Gas-Liquid Chromatography (GLC; amounts of SCFA in nmol/mg dry weight). The following SCFA were measured: propionate, butyrate, valerate and acetate.

The measure was made based on the following protocol: SCFA in an acid solution (pH 2.0 to 3.0) were separated on a GLC column coated with a polar stationary phase. This allowed for minimal preparation of the sample (no derivatisation) and straightforward basic FID detection. SCFA were extracted from caecum using an acid phosphate buffer containing HgCl2 for inactivation of any residual bacterial activity and an internal standard (2,2 Dimethyl-butyric acid) for GLC analysis. After centrifugation, the sterile-filtered supernatant was ready for analysis by GLC. SCFA were measured simultaneously.

Median ratio values were calculated in order to compare the different fiber-enriched diets on SCFA production.

Findings

The production of butyrate by BMOs enriched diet was significantly increased (see FIG. 3). Its production was increased by around 99% in comparison to the positive control. Its production was increased by 133% and by 136% in comparison to pectin and PDX, respectively.

The production of propionate by BMOs enriched diet was also significantly increased (see FIG. 4). Its production was increased by around 69% in comparison to the positive control. Its production was increased by 74% and by 75% in comparison to pectin and PDX, respectively.

These results are very surprising since pectin is usually seen as a high-inducer of SCFA (Stark et al, J Nutr. 1993, In vitro production of short-chain fatty acids by bacterial fermentation of dietary fiber compared with effects of those fibers on hepatic sterol synthesis in rats; Yang et al, Anaerobe, 2013, In vitro characterization of the impact of selected dietary fibers on fecal microbiota composition and short chain fatty acid production).

FIG. 5 represents the ratio of the median of each tested SCFA of each fiber-enriched diet divided by the median of the positive control diet (i.e. low-fiber diet only). A ratio of 1 (black line) means that there is no difference between the enriched diet and the control diet. A ratio below 1 means that the corresponding SCFA is higher in the control diet when compared to the fiber-enriched diet whereas a ratio above a means that the corresponding SCFA is higher with the fiber-enriched diet than the control. The PDX and Pectin enriched diets induced less SCFA release of all kinds. On the contrary the BMOS-enriched diet induces more SCFA release of all kinds (acetate, propionate, butyrate, valerate) than the low-fiber diet and than the other tested fibers. The BMOS-enriched diet was the only one to promote butyrate and propionate in such as high way.

The inventors therefore surprisingly found that mice fed with a specific BMO mixture were having a higher caecal (and therefore colonic) production for all the tested SCFA, and especially for butyrate and propionate.

The inventors therefore surprisingly found that mice fed with a composition comprising oligosaccharides as described in the present invention have a significantly higher caecal (and therefore colonic) propionate/butyrate production.

Due to the known beneficial properties of SCFA especially on eczema, a composition according to any of the two aspects described in the present invention would therefore be efficient in infants or young children for use in preventing and/or treating skin conditions and/or skin diseases.

The invention claimed is:

1. A method for treatment of atopic dermatitis in an infant or young child in need thereof by increasing short chain fatty acid (SCFA) production in the infant or young child, the method comprising administering a composition comprising an oligosaccharide mixture to the infant or young child in need thereof
the oligosaccharide mixture consists of 2'-fucosyllactose (2'FL) and lacto-N-neotetraose (LNnT) in a total amount of 0.1 to 10 wt. % of the composition,
the composition does not contain at least one of any galacto-oligosaccharide (GOS) or any bovine milk oligosaccharide (BMOS), and the composition does not contain any sialylated oligosaccharide.

2. The method according to claim 1, wherein the composition further comprises a probiotic bacterial strain selected from the group consisting of *Lactobacillus acidophilus, Lactobacillus salivarius, Lactobacillus rhamnosus, Lactobacillus paracasei, Lactobacillus casei, Lactobacillus johnsonii, Lactobacillus plantarum, Lactobacillus fermentum, Lactobacillus lactis, Lactobacillus delbrueckii, Lactobacillus helveticus, Lactobacillus bulgari, Lactococcus lactis, Lactococcus diacetylactis, Lactococcus cremoris, Streptococcus salivarius, Streptococcus thermophilus, Bifidobacterium lactis, Bifidobacterium animalis, Bifidobacterium longum, Bifidobacterium breve, Bifidobacterium infantis,* or *Bifidobacterium adolescentis* and mixtures thereof.

3. The method according to claim 1, wherein the composition does not contain any galacto-oligosaccharide (GOS).

4. The method according to claim 1, wherein the SCFA is butyrate.

5. The method according to claim 1, wherein the composition further comprises at least one fiber or precursor of a human milk oligosaccharide (HMO), the at least one fiber or precursor of HMO is selected from the group consisting of an inulin, polydextrose, a sialic acid, fucose and combinations thereof.

6. The method according to claim 1, wherein the composition is a nutritional composition.

7. The method according to claim 1, wherein the composition is a synthetic nutritional composition.

8. The method according to claim 1, wherein the composition does not contain any galacto-oligosaccharide (GOS) and does not contain any bovine milk oligosaccharide (BMOS).

9. The method according to claim 1, wherein the composition further comprises at least one precursor of a human milk oligosaccharide in an amount up to 3 g/L and selected from the group consisting of sialic acid, fucose and combinations thereof.

10. The method according to claim 1, wherein the composition further comprises from 10e3 to 10e12 CFU of a probiotic bacterial strain per g of the composition on a dry weight basis.

11. The method according to claim 1, wherein the composition further comprises at least one bacteriophage directed against pathogenic Streptococci, *Haemophilus, Moraxella* and Staphylococci.

12. The method according to claim 1, wherein the composition is administered in a form selected from the group consisting of an infant formula, a starter infant formula, a follow-on or follow-up formula, a baby food, an infant cereal composition, a human milk fortifier, a supplement, and combinations thereof.

13. The method according to claim 4, wherein the 2'FL and the LNnT are the oligosaccharides are the only oligosaccharides in the composition.

14. The method according to claim 1, wherein the oligosaccharide mixture consists of the 2'-fucosyllactose (2'FL) and the lacto-N-neotetraose (LNnT) in a weight ratio of 2FL:LNnT from 1:10 to 12:1.

15. The method according to claim 1, wherein the oligosaccharide mixture consists of the 2'-fucosyllactose (2'FL) and the lacto-N-neotetraose (LNnT) in a weight ratio of 2FL:LNnT from 1:5 to 1:0.5.

16. The method according to claim 1, wherein the oligosaccharide mixture consists of the 2'-fucosyllactose (2'FL) and the lacto-N-neotetraose (LNnT) in a total amount of 1 to 5 wt %.

17. The method according to claim 1, wherein the composition further comprises at least one precursor of a human milk oligosaccharide in an amount up to 0.2 g/L and selected from the group consisting of sialic acid, fucose and combinations thereof.

* * * * *